US006533820B2

(12) United States Patent
Dorigatti et al.

(10) Patent No.: US 6,533,820 B2
(45) Date of Patent: *Mar. 18, 2003

(54) BIOMATERIALS FOR BONE REPLACEMENTS

(75) Inventors: Franco Dorigatti, Trento (IT); Lanfranco Callegaro, Padua (IT); Aurelio Romeo, Rome (IT)

(73) Assignee: Fidia S.p.A., Abano Terme (IT)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/335,900

(22) Filed: Jun. 18, 1999

(65) Prior Publication Data

US 2001/0053938 A1 Dec. 20, 2001

(51) Int. Cl.[7] .................................................. A61F 2/28
(52) U.S. Cl. ................. 623/23.51; 623/23.58; 623/23.61; 523/116; 424/42.3
(58) Field of Search ................. 623/16, 23.51, 623/23.57, 23.58, 23.61; 433/180; 523/116; 424/423

(56) References Cited

U.S. PATENT DOCUMENTS

| 4,851,521 A |   | 7/1989  | della Valle et al.          |
|-------------|---|---------|-----------------------------|
| 4,904,257 A | * | 2/1990  | Mori et al. ......... 623/16 |
| 4,957,744 A |   | 9/1990  | della Valle et al.          |
| 5,356,629 A |   | 10/1994 | Sander et al.               |
| 5,676,964 A |   | 10/1997 | della Valle et al.          |
| 5,994,325 A | * | 11/1999 | Roufa et al. ......... 514/59 |
| 6,437,018 B1 | * | 8/2002 | Gertzman et al. ...... 523/116 |

FOREIGN PATENT DOCUMENTS

| EP | 0522569 A   | 1/1993  |
|----|-------------|---------|
| WO | WO 9117777 A | 11/1991 |

OTHER PUBLICATIONS

Abstract of JP 63229058, a Japanese Patent Application Published Sep. 22, 1988.

* cited by examiner

Primary Examiner—Paul Prebilic
(74) Attorney, Agent, or Firm—Birch, Stewart, Kolasch & Birch, LLP

(57) ABSTRACT

The present invention involves compositions for use as granular bone replacements. The compositions of the present invention are comprised of hyaluronic acid esters or salts of hyaluronic acid in association with a pharmacologically active compound wherein the molecular weight of the hyaluronic acid is below 250,000 and either artificial or natural bone granules. The present invention further involves a method of promoting the growth or repair of damaged or defective bones in either humans or animals using the compositions of hyaluronic acid derivatives and bone granules.

1 Claim, No Drawings

BIOMATERIALS FOR BONE REPLACEMENTS

This application is a continuation of co-pending application Ser. No. 08/318,859, filed on Dec. 19, 1994. Application Ser. No. 08/318,849 is the national phase of PCT International Application No. PCT/EP93/00933 filed on Apr. 16, 1993 under 35 U.S.C. §371. The entire contents of each of the above-identified applications are hereby incorporated by reference.

BACKGROUND OF THE INVENTION

1. Field of the Invention

The present invention relates to new biomaterials, i.e., bonding solutions for granular bone replacements and bone replacements in the form of pastes, comprising hyaluronic acid and hyaluronic acid derivatives.

2. Description of Related Art

Hyaluronic acid

Hyaluronic acid is a natural polysaccharide composed of alternating residues of D-glucuronic acid and N-acetyl-D-glucuronic acid. It is a linear polymer with a wide molecular weight range, depending on the source from which it is obtained, how it is prepared, and how the molecular weight is determined. In nature, it is present in the pericellular gel, in the fundamental substance of the connective tissues of vertebrates, of which it is the main component, in the synovial fluid of joints, in the vitreous humor, in umbilical cord tissues, and in the combs of domestic fowl.

Specific hyaluronic acid fractions with definite molecular weights are known which do not possess inflammatory activity, and which can therefore be used to enhance wound healing or substitute for endobulbar fluids, or which can be used in therapy for joint pathologies by intraarticular injection, as described in European Patent No. 0138572, granted to Applicants.

Also known are hyaluronic acid esters wherein all or part of the carboxy groups of the acid are esterified, and their use in the fields of pharmaceuticals, cosmetics, and biodegradable plastic materials, as described in U.S. Pat. Nos. 4,851,521 and 4,965,353 also granted to Applicants.

It is known that hyaluronic acid plays a fundamental role in tissue repair processes especially in the first stages of granulation tissue formation, stabilizing the coagulation matrix and controlling degradation, favoring the recruitment of inflammatory cells such as polymorphonucleocytes and monocytes, of mesenchymal cells such as fibroblasts and endothelial cells, and directing the subsequent migration of epithelial cells.

It is known that the application of hyaluronic acid solutions to bedsores, wounds and burns accelerates healing. The role of hyaluronic acid in the various stages of tissue repair has been described, by constructing a theoretical model, by Weigel P. H. et al.: "A model for the role of hyaluronic acid and fibrin in the early events during the inflammatory response and wound healing," *J. Theor. Biol.*, 119: 219, 1986.

Granular Bone Replacements

Granular bone replacements have been widely studied and used in dentistry and medicine owing to their biocompatible and osteoconductive properties, and because they easily fill cavities of various forms, such as those caused by alveolar bone shrinkage, postextraction cavities, and cystic cavities. The main difficulty when using this material is caused by its lack of binding properties, so that it easily becomes dislodged either during or after application. To overcome this drawback, various types of bonding materials have been proposed with which to prepare pastes containing bone granules. Fibrin is already being used, as described in patent applications JP A 60254640 and JP A 60254641.

One disadvantage of using fibrin as a bonding agent is that it can cause infection by the hepatitis virus, as well as by H.I.V. and other viruses, due to its human origin. Alternative materials have therefore been proposed, such as pullulan, chitin, glycol, carbomethylene chitin, and pectin, as described in patent application EP 0416398.

SUMMARY OF THE INVENTION

An object of the present invention is to provide a viscous solution composed of hyaluronic acid and/or hyaluronic acid esters or salts of hyaluronic acid in association with antibiotics, used singly or in combination, to bind bone replacements in granular form for use in dentistry or surgery of all kinds. Such solutions have excellent biocompatible and bioabsorbable characteristics, and are not liable to cause problems such as infection.

Another object of the present invention is to provide a paste comprising a viscous solution of hyaluronic acid and/or hyaluronic acid esters or salts of hyaluronic acid in association with antibiotics, used singly or in combination, and bone granules. The granules incorporated in the paste are firmly adhered together, thus facilitating their use in dentistry and bone surgery.

Further scope of the applicability of the present invention will become apparent from the detailed description provided below. However, it should be understood that the detailed description and specific examples, while indicating preferred embodiments of the invention, are given by way of illustration only, since various changes and modifications within the spirit and scope of the invention will become apparent to those skilled in the art from this detailed description.

DETAILED DESCRIPTION OF THE INVENTION

The following detailed description is provided to aid those skilled in the art in practicing the present inventions Even so, the following detailed description should not be construed to unduly limit the present invention, as modifications and variations in the embodiments herein discussed may be made by those of ordinary skill in the art without departing from the spirit or scope of the present inventive discovery.

The contents of each of the references cited herein are incorporated by reference in their entirety.

The foregoing objects are achieved by dissolving hyaluronic acid, esters of hyaluronic acid, or salts of hyaluronic acid in association with antibiotics, used singly or in combination, in water, to form highly viscous solutions. The viscosity of such solutions is at least 15 Pa.s, preferably over 22 Pa.s, at a temperature of 25° C. and 50%±5% relative humidity. The nearer the viscosity to the lower limit, the more liquid the solution; the greater the viscosity, the denser the solution. The correct degree of viscosity for ideal working conditions is a subjective parameter which depends on the individual, who can alter its viscosity by varying the concentration of the solution. The properties of the material comprising the solution, such as its molecular weight, will be selected according to the required degree of viscosity.

The solution according to the present invention is prepared by solubilizing hyaluronic acid, the partial ester of hyaluronic acid or a mixture of the same, or a salt of hyaluronic acid in association with an antibiotic or a mixture of the same, previously sterilized with gamma rays, in sterile water or buffer.

The esters of hyaluronic acid that can be used in the present invention are described in U.S. Pat. Nos. 4,851,521 and 4,965,353, and in PCT publication WO 92-13579. the salts of hyaluronic acid in association with antibiotics that can be used in the present invention are descried in U.S. Pat. No. 5,166,331. these can be used singly or in various combinations with one another, or with hyaluronic acid.

The powder is placed in the solubilization vessel under a sterile hood at a temperature of 25° C.±2° C. and 50%±5% humidity. Solubilization can be achieved in a mixer composed of two spiral elements turning in opposite directions.

Operative conditions depend on the desired viscosity and can be as follows:

| FINAL VISCOSITY | SOLUBILIZATION TEMPERATURE | NO. TURNS IN MIXER | SOLUBILIZATION DURATION |
|---|---|---|---|
| 15 Pa · s | 30° C. ± 5° C. | 60 rpm | 4 Hours |
| 22 Pa · s | 45° C. ± 5° C. | 40 rpm | 8 Hours |

All air is eliminated from the solution before use by placing it in a vacuum for two hours (minimum 0.01 mbar). It is possible to sterilize a solution prepared with non-sterile material by filtering it through a filter with a pore size of 0.22 μm. In this case, to facilitate filtration, the solution can first be prepared at a lower viscosity than will be required for its application. It is then filtered and subsequently distilled under vacuum until it reaches the concentration corresponding to the desired viscosity. Solutions thus prepared can be mixed with bone granules to form a paste to be used to fill bone cavities and defects. The ratio between the quantity of solution and the quantity of granules is 1:3, w/w, or more. If the quantity of solution is too small, the granules will not be sufficiently bound together, so more solution rust be added. If the paste is too liquid for easy application, it can be placed in a high vacuum for about two minutes, repeating this operation until the correct consistency is obtained.

The bone granules that can be used in the present invention are not particularly limited. In general, it is possible to use those already in common use. Examples of these can be found in U.S. Pat. Nos. 4,693,986 and 4,629,464. The diameter of the granules can be between 50 μm and 5 mm, and they can be porous or nonporous. Among the materials preferred due to their biocompatibility are granules of hydroxyapatite, tricalcium phosphate, and calcium carbonate.

For purely illustrative purposes, described hereafter are some examples of preparations of solutions and pastes according to the present invention.

The Esters of Hyaluronic Acid

Esters of hyaluronic acid useful in the present invention are esters of hyaluronic acid with aliphatic, araliphatic, cycloaliphatic or heterocyclic alcohols, in which are esterified all (so-called "total esters") or only a part (so-called "partial esters") of the carboxylic groups of the hyaluronic acid, and salts of the partial esters with metals or with organic bases, biocompatible or acceptable from a pharmacological point of view.

The useful esters include esters which derive from alcohols which themselves possess a notable pharmacological action. The saturated alcohols of the aliphatic series or simple alcohols of the cycloaliphatic series are useful in the present invention.

In the above mentioned esters in which some of the carboxylic acid groups remain free (i.e., partial esters), these may be salified with metals or organic bass, such as with alkaline or alkaline earth metals or with ammonia or nitrogenous organic bases.

Most of the esters of hyaluronic acid ("HY"), unlike HY itself, present a certain degree of solubility in organic solvents. This solubility depends on the percentage of esterified carboxylic groups and on the type of alkyl group linked with the carboxyl. Therefore, an HY compound with all its carboxylic groups esterified presents, at room temperature, good solubility for example in dimethylsulfoxide (the benzyl ester of HY dissolves in DMSO in a measure of 200 mg/ml). Most of the total esters of HY present also, unlike HY and especially its salts, poor solubility in water and are essentially insoluble in water. The solubility characteristics, together with particular and notable viscoelastic properties, make the HY esters particularly preferred for use in composite membranes.

Alcohols of the aliphatic series to be used as esterifying components of the carboxylic groups of hyaluronic acid for use in composite membranes according to the present invention are for example those with a maximum of 34 carbon atoms, which may be saturated or unsaturated and which may possibly also be substituted by other free functional or functionally modified groups, such as amine, hydroxyl, aldehyde, ketone, mercaptan, or carboxyl groups or by groups derived from these, such as hydrocarbyl or di-hydrocarbylamine groups (from now on the term "hydrocarbyl" will be used to refer not only to monovalent radicals of hydrocarbons such as the $C_nH_{2n+1}$ type, but also bivalent or trivalent radicals, such as "alkylenes" $C_nH_{2n}$ or "alkylidenes" $C_nH_{2n}$), ether or ester groups, acetal or ketal groups, thioether or thioester groups, and esterified carboxyl or carbamide groups and carbamide substituted by one or more hydrocarbyl groups, by nitrile groups or by halogens.

Of the above mentioned groups containing hydrocarbyl radicals, these are preferably lower aliphatic radicals, such as alkyls, with a maximum of 6 carbon atoms. Such alcohols may also be interrupted in the carbon atom chain by heteroatoms, such as oxygen, nitrogen and sulfur atoms. Preferred are alcohols substituted with one or two of the said functional groups.

Alcohols of the above mentioned group which are preferably used are those with a maximum of 12, and especially 6 carbon atoms, and in which the hydrocarbyl atoms in the above mentioned amine, ether, ester, thioether, thioester, acetal, ketal groups represent alkyl groups with a maximum of 4 carbon atoms, and also in the esterified carboxyl or substituted carbamide groups the hydrocarbyl groups are alkyls with the same number of carbon atoms, and in which in the amine or carbamide groups way be alkylenamine or alkylencarbamide groups with a maximum of 8 carbon atoms. Of these alcohols, specifically preferred are saturated and non-substituted alcohols, such as the methyl, ethyl, propyl, and isopropyl alcohols, normal butyl alcohol, isobutyl alcohol, tertiary butyl alcohol, the amyl, pentyl, hexyl, octyl, nonyl and dodecyl alcohols and, above all, those with a linear chain, such as normal octyl and dodecyl alcohols. Of the substituted alcohols of this group, the bivalent alcohols are useful, such as ethyleneglycol, propyleneglycol and butyleneglycol, the trivalent alcohols such as glycerine, the aldehyde alcohols such as tartronic alcohol, the carboxylic alcohols such as lactic acids, for example glycolic acid, malic acid, the tartaric acids, citric acid, the aminoalcohols, such as normal aminoethanol, aminopropanol, normal aminobutanol and their diaethylated and diethylated derivatives in the amine function, choline, pyrrolidinylethanol, piperidinylethanol, piperazineylethanol and the corresponding derivatives of normal propyl or normal butyl alcohol, monothicethyleneglycol or its alkyl derivatives, such as the ethyl derivative in the mercaptan function.

Of the higher saturated aliphatic alcohols, preferred are cetyl alcohol and myricyl alcohol, but for the aim of the present invention the higher unsaturated alcohols with one or two double bonds, are especially important, such as especially those contained in many essential oils and with affinity to terpene, such as citronellol, geraniol, nerol, nerolidol, linalool, farnesol, phytol. of the unsaturated lower alcohols it is necessary to consider allyl alcohol and propargyl alcohol. Of the araliphatic alcohols, preferred are those with only one benzene residue and in which the aliphatic chain has a maximum of 4 carbon atoms, which the benzene residue can be substituted by between 1 and 3 methyl or hydroxyl groups or by halogen atoms, especially by chlorine, bromine and iodine, and in which the aliphatic chain may be substituted by one or more functions chosen from the group containing fee amine groups or mono- or dimethylated or by pyrrolidine or piperidine groups. Of these alcohols, most preferred are benzyl alcohol and phenetyl alcohol.

The alcohols of the cycloaliphatic or aliphatic-cycloaliphatic series may derive from mono- or polycyclic hydrocarbons, may preferably have a maximum of 34 carbon atoms, may be unsubstituted and may contain one or more substituents, such as those mentioned above for the aliphatic alcohols. Of the alcohols derived from cyclic monoannular hydrocarbons, preferred are those with a maximum of 12 carbon atoms, the rings with preferably between 5 and 7 carbon atoms, which may be substituted for example by between one and three lower alkyl groups, such as methyl, ethyl, propyl or isopropyl groups. As specific alcohols of this group the following are most preferred: cyclohexanol, cyclohexanediol, 1,2,3-cyclohexanetroil and 1,3,5-cyclohexanetriol (phloroglucitol), inositol, and the alcohols which derive fron p-methane such as carvomenthol, menthol, and α-γterpineol, 1-terpineol, 4-terpineol and piperitol, or the mixture of these alcohols known as "terpineol", 1,4- and 1,8 terpin. Of the alcohols which derive from hydrocarbons with condensed rings, such as those of the thujane, pinane or comphane, the following are preferred: thujanol, sabinol, pinol hydrate, D and L-borneol and D and L-isoborneol.

Aliphatic-cycloaliphatic polycyclic alcohols to be used for the esters of the present invention are sterols, cholic acids and steroids, such as sexual hormones and their synthetic analogues, especially corticosteroids and their derivatives. It is therefore possible to use: cholesterol, dihydrocholesterol, epidihydrocholesterol, coprostanol, epicoprostanol, sitosterol, stigmasterol, ergosterol, cholic acid, deoxycholic acid, lithocholic acid, estriol, estradiol, equilenin, equilin and their alkylate derivatives, as well as their ethynyl or propynyl derivatives in position 17, such as 17α-ethynl-estradiol or 7α-methyl-17α-ethynyl-estradiol, pregnenolone, pregnanediol, testosterone and its derivatives, such as 17α-methyltestosterone, 1,2-dehydrotestosterone and 17α-methyl-1,2-dehydrotestosterone, the alkynylate derivatives in position 17 of testosterone and 1,2-dehydrotestosterone, such as 17α-ethynyltestosterone, 17α-propynyltestosterone, norgestrel, hydroxyprogesterone, corticosterone, deoxycorticosterone, 19-nortestosterone, 19-nor-17α-methyltestosterone and 19-nor-17α-ethynyltestosterone, antihormones such as cyproterone, cortisone, hydrocortisone, prednisone, prednisolone, fluorocortisone, dexamethasone, betametbasone, paramethasone, flumethasone, fluocinolone, fluprednylidene, clobetasol, beclomethasone, aldosterone, deoxycorticosterone, alfaxolone, alfadolone, and bolasterone. As esterifying components for the esters of the present invention the following are useful: genins (aglycons) of the cardioactive glucosides, such as digitoxigenin, gitoxigenin, digoxigenin, strophanthidin, tigogenin and saponins.

Other alcohols to be used according to the invention are the vitamin ones, such as axerophthol, vitamins $D_2$ and $D_3$, aneurine, lactoflavine, ascorbic acid, riboflavine, thiamine, and pantothenic acid.

Of the heterocyclic acids, the following can be considered as derivatives of the above mentioned cycloaliphatic or aliphatic-cycloaliphatic alcohols if their linear or cyclic chains are interrupted by one or more, for example by between one and three heteroatoms, for instance chosen from the group formed by —O—, —S—, —N, and —NH—, and in these, there may be one or more unsaturated bonds, for example double bonds, in particular between one and three, thus including also heterocyclic compounds with aromatic structures. For example the following should be mentioned: furfuryl alcohol, alkaloids and derivatives such as atropine, scopolamine, cinchonine, 1a cinchonidine, quinine, morphine, codeine, nalorphine, N-butylscopolammonium bromide, ajmaline; phenylethylamines such as ephedrine, isoproterenol, epinephrine; phenothiazine drugs such as perphenazine, pipothiazine, carphenazine, homofenazine, acetophenazine, fluophenazine, and N-hydroxyethylpromethazine chloride; thioxanthene drugs such as flupenthixol and clopenthixol; anticonvulsants such as meprophendiol; antipsychotics such as opipramol; antiemetics such as oxypendyl; analgesics such as carbetidine and phenoperidine and methadol; hypnotics such as etodroxizine; anorexics such as benzidrol and diphemethoxidine; minor tranquilizers such as hydroxyzine; muscle relaxants such as cinnamedrine, diphylline, mephenesin, methocarbamol, chlorphenesin, 2,2-diethyl-1, 3-propanediol, guaifenesin, hydrocilamide; coronary vasodilators such as dipyridamole and oxyfedrine; adrenergic blockers such as propanolol, timolol, pindolol, bupranolol, atenolol, metroprolol, practolol; antineoplastics such as 6-azauridine, cytarabine, floxuridine; antibiotics such as chloramphenicol, thiamphenicol, erythromycin, oleandomycin, lincomycin; antivirals such as idoxuridine; peripheral vasodilators such as isonicotinyl alcohol; carbonic anhydrase inhibitors such as sulocarbilate; antiasthmatic and antiinflammatories such as tiaramide; sulfamidics such as 2-p-sulfanilonoethanol.

In some cases hyaluronic acid esters may be of interest where the ester groups derive from two or more therapeutically active hydroxylic substances, and naturally all possible variants may be obtained. Especially interesting are the substances in which two types of different ester groups deriving from drugs of a hydroxylic character are present and in which the remaining carboxyl groups are free, salified with metals or with a base, possibly also the bases being themselves therapeutically active, for example with the same or similar activity as that of the esterifying component. In particular, it is possible to have hyaluronic esters deriving on the one hand from an antiinflammatory steroid, such as one of those mentioned previously, and on the other hand from a vitamin, from an alkaloid or from an antibiotic, such as one of those listed.

Method of Preparing HY Esters of the Invention

Method A:

The esters of hyaluronic acid may be prepared by methods known per se for the esterification of carboxylic acids, for example by treatment of free hyaluronic acid with the desired alcohols in the presence of catalyzing substances, such as strong inorganic acids or ionic exchangers of the acid type, or with an etherifying agent capable of introducing the desired alcoholic residue in the presence of inorganic or organic bases. As esterifying agents it is possible to use those known in literature, such as especially the esters of various inorganic acids or of organic sulphonic acids, such as hydracids, that is hydrocarbyl halogenides, such as methyl or ethyl iodide, or neutral sulphates or hydrocarbyl acids, alfites, carbonates, silicates, phosphites or hydrocarbyl sulfonates, such as methyl benzene or p-toluene-sulfonate or methyl or ethyl chlorosulfonate. The reaction may take place in a suitable solvent, for example an alcohol, preferably that corresponding to the alkyl group to be introduced in the carboxyl group. But the reaction may also take place in non-polar solventss, such as ketones, ethers, such as dioxane or aprotic solvents, such as dimethyl-sulphoxide. As a base it is possible to use for example a hydrate of an alkaline or alkaline earth metal or magnesium or silver oxide or a basic salt or one of these metals, such as a carbonate, and, of the organic bases, a tertiary azotized base, such as pyridine or collidine. In the place of the base it is also possible to use an ionic exchanger of the basic type.

Another esterification method employs the metal salts or salts with organic azotized bases, for example ammonium or ammonium substitute salts. Preferably, the salts of the alkaline or alkaline earth metals are used, but also any other metallic salt may be used. The esterifying agents are also in this case those mentioned above and the same applies to the solvents. It is preferable to use aprotic solvents, for example dimethylsulphoxide and dimethylformamide.

In the esters obtained according to this procedure or according to the other procedure described hereafter, free carboxylic groups of the partial esters may be salified, if desired, in a per se known manner.

Method B:

The hyaluronic esters may also be prepared by a method which consists of treating a quaternary ammonium salt of hyaluronic acid with an etherifying agent, preferably in an aprotic organic solvent.

As organic solvents it is preferable to use aprotic solvents, such as dialkylsulphoxides, dialklcarboxamides, such as in particular lower alkyl dialkylsulphoxides, especially dimethyl-sulphoxide, and lower alkyl dialkylamides of lower aliphatic acids, such as dimethyl or diethyl-formamide or dimethyl or diethylacetamide.

Other solvents however are to be considered which are not always aprotic, such as alcohols, ethers, ketones, esters, especially aliphatic or heterocyclic alcohols and ketones with a lower boiling point, such as hexafluoroisopropanol, trifluoroethanol, and N-methylpyrrolidone.

The reaction is effected preferably at a temperature range of between about 0° C. and 100° C., especially between about 25° C. and 75° C., for example at about 30° C.

The esterification is carried out preferably by adding by degrees the esterifying agent to the above mentioned ammonium salt to one of the above mentioned solvents, for example to dimethyl-sulphoxide.

As an alkylating agent it is possible to use those mentioned above, especially the hydrocarbyl halogens, for example alkyl halogens. As starting quaternary ammonium salts it is preferable to use the lower ammonium tetraalkylates, with alkyl groups preferably between 1 and 6 carbon atoms. Mostly, hyaluronate of tetrabutylammonium is used. It is possible to prepare these quaternary ammonium salts by reacting a metallic salt of hyaluronic acid, preferably one of those mentioned above, especially sodium or potassium salt, in aqueous solution with a salified sulphonic resin with a quaternary ammonium base.

One variation of the previously described procedure consists in reacting a potassium or sodium salt of hyaluronic acid, suspended in a suitable solution such as dimethylsulphoxide, with a suitable alkylating agent in the presence of catalytic quantities of a quaternary ammonium salt, such as iodide of tetrabutylammonium.

For the preparation of the hyaluronic acid eaters, it is possible to use hyaluronic acids of any origin, such as for example the acids extracted from the above mentioned natural starting materials,, for example from cocks' combs. The preparation of such acids is described in literature: preferably, purified hyaluronic acids are used. Especially used are hyaluronic acids comprising molecular fractions of the integral acids obtained directly by extraction of the organic materials with molecular weights varying within a wide range, for example from about 90%–80% (MW=11.7–10.4 million) to 0.2% (MW=30,000) of the molecular weight of the integral acid having a molecular weight of 13 million, preferably between 5% and 0.2%. Such fractions may be obtained with various procedures described in literature, such as by hydrolyzing, oxydizing, enzymatic or physical procedures, such as mechanical or radiational procedures. Primordial extracts are therefore often formed during these same by publication procedures (for example see the article by Balazs et al. quoted above in "Cosmetics & Toiletries"). The separation and purification of the molecular fractions obtained are brought about by known techniques, for example by molecular filtration.

Additionally useful are purified fractions obtainable from hyaluronic acid, such as for example the ones described in European Patent Publn. No. 0138572.

The salification of HY with the above metals, for the preparation of starting salts for the particular esterification procedure described above, is performed in a per se known manner, for example by reacting HY with the calculated base quantity, for example with alkaline hydrates or with basic salts of such metals, such as carbonates or bicarbonates.

In the partial esters it is possible to salify all the remaining carboxylic groups or only part of them, dosing the base quantities so as to obtain the desired stoichiometric degree of salification. With the correct degree of salification it is possible to obtain esters with a wide range of different dissociation constants and which therefore give the desired pH, in solution or "in situ" at the time of therapeutic application.

PREPARATION EXAMPLES

The following exemplify the preparation of hyaluronic acid esters useful in the composite membranes of the present invention.

Example 1

Preparation of the (partial) propyl ester of hyaluronic acid (HY)

—50% of the esterified carboxylic groups

—50% of the salified carboxylic groups (Na)

12.4 g of HY tetrabutylammonium salt with a molecular weight 170,000 corresponding to 20 m.Eq. of a monomeric unit are solubilized in 620 ml of dimethylsulfoxide at 25° C., 1.8 g (10.6 m.Eq.) of propyl iodide are added and the resulting solution is kept at a temperature of 30° for 12 hours.

A solution containing 62 ml of water and 9 g of sodium chloride is added and the resulting mixture is slowly poured into 3,500 ml of acetone under constant agitation. A precipitate is formed which is filtered and washed three times with 500 ml of acetone/water 5:1 and three times with acetone and finally vacuum dried for eight hours at 30° C.

The product is then dissolved in 550 ml of water containing 1% of sodium chloride and the solution is slowly poured into 3,000 ml of acetone under constant agitation. A precipitate is formed which is filtered and washed twice with 500 ml of acetone/water (5:1) and three times with 500 ml of acetone and finally vacuum dried for 24 hours at 30° C. 7.9 g of the partial propyl ester compound in the title are obtained. Quantitative determination of the ester groups is carried out using the method of R. H. Cundiff and P. C. Markunas [Anal. Chem. 33, 1028–1030, (1961)].

Example 2
Preparation of the (partial) isopropyl ester of hyaluronic acid (HY)—50% of esterified caboxylic groups—50% of salified carboxylic groups (Na)

12.4 g of HY tetrabutylammonium salt with a molecular weight of 160,000 corresponding to 20 m.Eq. of a monomeric unit are solubilized in 620 ml of dimethylsulfoxide at 25° C., 1.8 g (10.6 m.Eq.) of isopropyl iodide are added and the resulting solution is kept for 12 hours at 30° C.

A solution containing 62 ml of water and 9 g of sodium chloride is added and the resulting mixture is slowly poured into 3,500 ml of acetone under constant agitation. A precipitate is formed which is filtered and washed three times with 500 ml of acetone/water 5:1 and three times with acetone and finally vacuum dried for eight hours at 30° C.

The product is then dissolved in 550 ml of water containing 1% of sodium chloride and the solution is slowly poured into 3,000 ml of acetone under constant agitation. A precipitate is formed which is filtered and washed twice with 500 ml of acetone/water 5:1 and three times with 500 ml of acetone and finally vacuum dried for 24 hours at 30° C. 7.8 g of the partial isopropyl ester compound in the title are obtained. Quantitative determination of the ester groups is carried out using the method of R. H. Cundiff and P. C. Markunas [Anal. Chem. 33, 1028–1030 (1961)].

Example 3
Preparation of the (partial) ethyl ester of hyaluronic acid (HY)—75% of esterified carboxylic groups—25% of salified carboxylic groups (Na)

12.4 g of HY tetrabutylammonium salt with a molecular weight of 250,000 corresponding to 20 m.Eq. of a monomeric unit are solubilized in 620 ml of dimethylsulfoxide at 25° C., 2.5 g (15.9 m.Eq.) of ethyl iodide are added and the resulting solution is kept for 12 hours at 30° C.

A solution containing 62 ml of water and 9 g of sodium chloride is added and the resulting mixture is slowly poured into 3,500 ml of acetone under constant agitation. A precipitate is formed which is filtered and washed three times with 500 ml of acetone/water 5:1 and three times with acetone and finally vacuum dried for eight hours at 30° C.

The product is then dissolved in 550 ml of water containing 1% of sodium chloride and the solution is slowly poured into 3,000 ml of acetone under constant agitation. A precipitate is formed which is filtered and washed twice with 500 ml of acetone/water 5:1 and three times with 500 ml of acetone and finally vacuum dried for 24 hours at 30° C. 7.9 g of the partial ethyl ester compound in the title are obtained. Quantitative determination of the ester groups is carried out using the method of R. H. Cundiff and P. C. Markunas [Anal. Chem. 33, 1028–1030, (1961)].

Example 4
Preparation of the (partial) methyl ester of hyaluronic acid (HY)—75% of esterified carboxylic groups—25% of salified carboxylic groups (Na)

12.4 g of HY tetrabutylamonium salt with a molecular weight of 80,000 corresponding to 20 m.Eq. of a monomeric unit are solubilized in 620 ml of dimethylsulfoxide at 25° C., 2.26 g (15.9 m.Eq.) of methyl iodide are added and the resulting solution is kept for 12 hours at 30° C.

A solution containing 62 ml of water and 9 g of sodium chloride is added and the resulting mixture is slowly poured into 3,500 ml of acetone under constant agitation. A precipitate is formed which is filtered and washed three times with 500 ml of acetone/water 5:1 and three times with acetone and finally vacuum dried for eight hours at 30° C.

The product is then dissolved in 550 ml of water containing 1% of sodium chloride and the solution is slowly poured into 3,000 ml of acetone under constant agitation. A precipitate is formed which is filtered and washed twice with 500 ml of acetone/water 5:1 and three times with 500 ml of acetone and finally vacuum dried for 24 hours at 30° C. 7.8 g of the partial methyl ester compound in the title are obtained. Quantitative determination of the ester groups is carried out using the method of R. H. Cundiff and P. C. Markunas [Anal. Chem. 33, 1028–1030 (1961)].

Example 5
Preparation of the methyl ester of hyaluronic acid (HY)

12.4 g of HY tetrabutylamonium salt with a molecular weight of 120,000 corresponding to 20 m.Eq. of a monomeric unit are solubilized in 620 ml of dimethylsulfoxide at 25° C., 3 g (21.2 m.Eq.) of methyl iodide are added and the solution is kept for 12 hours at 30° C.

The resulting mixture is slowly poured into 3,500 ml of ethyl acetate under constant agitation. A precipitate is formed which is filtered and washed four times with 500 ml of ethyl acetate and finally vacuum dried for twenty four hours at 30° C.

8 g of the ethyl ester product in the title are obtained. Quantitative determination of the ester groups is carried out using the method of R. H. Cundiff and P. C. Markunas [Anal. Chem. 33, 1028–1030 (1961)].

Example 6
Preparation of the ethyl ester of hyaluronic acid (HY)

12.4 g of HY tetrabutylammonium salt with a molecular weight of 85,000 corresponding to 20 m.Eq$_4$ of a monomeric unit are solubilized in 620 ml of dimethylsulfoxide at 25° C., 3.3 g (21.2 m.Eq., of ethyl iodide are added and the solution is kept for 12 hours at 30° C.

The resulting mixture is slowly poured into 3,500 ml of ethyl acetate under constant agitation. A precipitate is formed which is filtered and washed four times with 500 ml of ethyl acetate and finally vacuum dried for twenty-four hours at 30° C.

8 g of the ethyl ester product in the title are obtained. Quantitative determination of the ester groups is carried out using the method of R. H. Cundiff and P. C. Markunas [Anal. Chem. 33, 1028–1030 (1961)].

Example 7
Preparation of the propyl ester of hyaluronic acid (HY)

12.4 g of HY tetrabutylammonium salt with a molecular weight of 170,000 corresponding to 20 m.Eq. of a monomeric unit are solubilized in 620 ml of dimethylsulfoxide at 25° C., 3.6 g (21.2 m.Eq.) of propyl iodide are added and the solution is kept for 12 hours at 30° C.

The resulting mixture is slowly poured into 3,500 ml of ethyl acetate under constant agitation. A precipitate is formed which is filtered and washed four times with 500 ml of ethyl acetate and finally vacuum dried for twenty-four hours at 30° C.

8.3 g of the propyl ester product in the title are obtained. Quantitative determination of the ester groups is carried out using the method of R. H. Cundiff and P. C. Markunas [Anal. Chem. 33, 1028–1030 (1961)].

Example 8

Preparation of the (partial) butyl ester of hyaluronic acid (HY)—50% of esterified carboxylic groups—50% of salified carboxylic groups (Na)

12.4 g of HY tetrabutylammonium salt with a molecular weight of 620,000 corresponding to 20 m.Eq. of a monomeric unit are solubilized in 620 ml of dimethylsulfoxide at 25° C., 1.95 g (10.6 m.Eq.) of n-butyl iodide are added and the resulting solution is kept for 12 hours at 30° C.

A solution containing 62 ml of water and 9 g of sodium chloride is added and the resulting mixture is slowly poured into 3,500 ml of acetone under constant agitation. A precipitate is formed which is filtered and washed three times with 500 ml of acetone/water 5:1 and three times with acetone and finally vacuum dried for eight hours at 30° C.

The product is then dissolved in 550 ml of water containing 1% of sodium chloride and the solution is slowly poured into 3,000 ml of acetone under constant agitation. A precipitate is formed which is filtered and washed twice with 500 ml of acetone/water 5:1 and three times with 500 ml of acetone and finally vacuum dried for 24 hours at 30° C. 8 g of the partial butyl ester compound in the title are obtained. Quantitative determination of the ester groups is carried out using the method of R. H. Cundiff and P. C. Markunas [Anal. Chem. 33, 1028–1030 (1961)].

Example 9

Preparation of the (partial) ethoxy-carbonylmethyl ester of hyaluronic acid (HY)—75% of esterified carboxylic groups—25% of salified carboxylic groups (Na)

12.4 g of HY tetrabutylammonium salt with a molecular weight of 180,000 corresponding to 20 m.Eq. of a monomeric unit are solubilized in 620 ml of dimethylsulfoxide at 25° C., 2 g of tetrabutylmmonium iodide and 1.84 g (15 m.Eq.) of ethyl chloroacetate are added and the resulting solution of kept for 24 hours at 30° C.

A solution containing 62 ml of water and 9 g of sodium chloride is added and the resulting mixture is slowly poured into 3,500 ml of acetone under constant agitation. A precipitate is formed which is filtered and washed three times with 500 ml of acetone/water 5:1 and three times with acetone and finally vacuum dried for eight hours at 30° C.

The product is then dissolved in 550 ml of water containing 1% of sodium chloride and the solution is slowly poured into 3,000 ml of acetone under constant agitation. A precipitate is formed which is filtered and washed twice with 500 ml of acetone/water 5:1 and three times with 500 ml of acetone and finally vacuum dried for 24 hours at 30° C. 10 g of the partial ethoxycarbonyl methyl ester compound in the title are obtained.

Quantitative determination of the ethoxylic ester groups is carried out using the method of R. E. Cundiff and P. C. Markunas [Anal. Chem. 33, 1028–1030 (1961)].

Example 10

Preparation of the n-pentyl ester of hyaluronic acid (HY)

12.4 g of HY tetrabutylammonium salt with a molecular weight of 620,000 corresponding to 20 m.Eq. of a monomeric unit are solubilized in 620 ml of dimethylsulfoxide at 25° C., 3.8 g (25 m.Eq.) of n-pentyl bromide and 0.2 g of iodide tetrabutyl-ammonium are added, the solution is kept for 12 hours at 30° C.

The resulting mixturte is slowly poured into 3,500 ml of ethyl acetate under constant agitation. A precipitate is formed which is filtered and washed four times with 500 ml of ethyl acetate and finally vacuum dried for twenty four hours at 30° C.

8.7 g of the n-pentyl ester product in the title are obtained. Quantitative determination of the ester groups is carried out using the method described on pages 169–172 of Siggia S. and Hann J. G. "Quantitative organic analysis via functional groups" 4th Edition, John Wiley and Sons.

Example 11

Preparation of the isopentyl ester of hyaluronic acid (HY)

12.4 g of HY tetrabutylammonium salt with a molecular weight of 170,000 corresponding to 20 m.Eq. of a monomeric unit are solubilized in 620 ml of dimethysulfoxide at 25° C., 3.8 g (25 m.Eq.) of isopentyl bromide and 0.2 g of tetrabutylwmmonium iodide are added, the solution is kept for 12 hours at 30° C.

The resulting mixture is slowly poured into 3,500 ml of ethyl acetate under constant agitation. A precipitate is formed which is filtered and washed four times with 500 ml of ethyl acetate and finally vacuum dried for twenty four hours at 30° C.

8.6 g of the isopentyl ester product featured in the title are obtained. Quantitative determination of the ester groups is carried out according to the method described on pages 169–172 of Siggia S. and Hanna J. G. "Quantitative organic analysis via functional groups" 4th Edition, John Wiley and Sons.

Example 12

Preparation of the benzylester of hyaluronic acid (HY)

12.4 g of HY tetrabutylammonium salt with a molecular weight of 170,000 corresponding to 20 m.Eq. of a monomeric unit are solubilized in 620 ml of dimethylsulfoxide at 25° C. 4.5 g (25 m.Eq.) of benzyl bromide and 0.2 g of tetrabutylammonium iodide are added, the solution is kept for 12 hours at 30° C.

The resulting mixture is slowly poured into 3,500 ml of ethyl acetate under constant agitation. A precipitate is formed which is filtered and washed four times with 500 ml of ethyl acetate and finally vacuum dried for twenty four hours at 30° C.

9 g of the benzyl ester product in the title are obtained. Quantitative determination of the ester groups is carried out according to the method described on pages 169–172 of Siggia S. and Hanna J. G. "Quantitative organic analysis via functional groups" 4th Edition, John Wiley and Sons.

Example 13

Preparation of the β-phenylethyl ester of hyaluronic acid (HY)

12.4 g of HY tetrabutylamonium salt with a molecular weight of 125,000 corresponding to 20 m.Eq. of a monomeric unit are solubilized in 620 ml of dimethylsulfoxide at 25° C., 4.6 g (25 m.Eq.) of 2-bromoethylbenzene and 185 mg of tetrabutylammonium iodide are added, and the solution is kept for 12 hours at 30° C.

The resulting mixture is slowly poured into 3,500 ml of ethyl acetate under constant agitation. A precipitate is thus formed which is then filtered and washed four times with 500 ml of ethyl acetate and finally vacuum dried for twenty four hours at 30° C.

9.1 g of the β-phenylethyl ester in the title are obtained. Quantitative determination of the ester groups is carried out according to the method described on page 168–172 of Siggia S. and hanna J. G. "Quantitative organic analysis via functional groups" 4th Edition, John Wiley and Sons.

Example 14
Preparation of the benzyl ester of hyaluronic acid (HY)

3 g of the potassium salt of HY with a molecular weight of 162,000 are suspended in 200 ml of dimethylsulfoxide; 120 mg of tetrabutylammonium iodide and 2.4 g of benzyl bromide are added.

The suspension is kept in agitation for 48 hours at 30° C. The resulting mixture is slowly poured into 1,000 ml of ethyl acetate under constant agitation. A precipitate is formed which is filtered and washed four times with 150 ml of ethyl acetate and finally vacuum dried for twenty four hours at 30° C.

3.1 g of the benzyl ester product in the title are obtained. Quantitative determination of the ester groups is carried out according to the method described on pages 169–172 of Siggia S. and Hanna J. G. "Quantitative organic analysis via functional groups" 4th Edition, John Wiley and Sons.

Example 15
Preparation of the (partial propyl) ester of hyaluronic acid (HY)—85% of esterified carboxylic groups—15% of salified carboxylic groups (Na)

12.4 g of HY tetrabutylamonium salt with a molecular weight of 165,000 corresponding to 20 m.Eq. of a monomeric unit are solubilized in 620 ml of dimethysulfoxide at 25° C., 2.9 g (17 m.Eq.) of propyl iodide are added and the resulting solution is kept for 12 hours at 30° C.

A solution is then added containing 62 ml of water and 9 g of sodium chloride and the resulting mixture is slowly poured into 3,500 ml of acetone under constant agitation. A precipitate is formed which is filtered and washed three times with 500 ml of acetone/water 5:1 and three times with acetone and finally vacuum dried for eight hours at 30° C.

The product is then dissolved in 550 ml of water containing 1.% of sodium chloride and the solution is slowly poured into 3,000 ml of acetone under constant agitation. A precipitate is formed which is filtered and washed twice with 500 ml of acetone/water 5:1 and three times with 500 ml of acetone and finally vacuum dried for 24 hours at 30° C. 8 g of the partial propyl ester compound in the title are obtained. Quantitative determination of the ester groups is carried out using the method of R. H Cundiff and P. C. Markunas [Anal. Chem. 33, 1028–1030 (1961)].

Example 16
Preparation of the n-octyl ester of hyaluronic acid (HY)

12.4 g of HY tetrabutylammonium salt with a molecular weight of 170,000 corresponding to 20 m.Eq. of a monomeric unit are solubilized in 620 ml of dimethylsulfoxide at 25° C., 4.1 g (21.2 m.Eq.) of 1-bromooctane are added and the solution is kept for 12 hours at 30° C.

The resulting mixture is slowly poured into 3,500 ml of ethyl acetate under constant agitation. A precipitate is formed which is filtered and washed four times with 500 ml of ethyl acetate and finally vacuum dried for 24 hours at 30° C. 9.3 g of the octyl ester product in the title are obtained. Quantitative determination of the ester groups is carried out using the method described in Siggia S. and Hanna J. G. "Quantitative organic analysis via functional groups", 4th Edition, John Wiley and Sons, pages 169–172.

Example 17
Preparation of the isopropyl ester of hyaluronic acid (HY)

12.4 g of HY tetrabutylammonium salt with a molecular weight of 170,000 corresponding to 20 m.Eq. of a monomeric unit are solubilized in 620 ml of dimethylsulfoxide at 25° C., 2.6 g (21.2 m.Eq.) of isopropyl bromide are added and the solution is kept for 12 hours at 30° C.

The resulting mixture is slowly poured into 3,500 ml of ethyl acetate under constant agitation. A precipitate is formed which is filtered and washed four times with 500 ml of ethyl acetate and finally vacuum dried for 24 hours at 30° C. 8.3 g of the isopropyl ester product in the title are obtained. Quantitative determination of the ester groups is carried out using the method of R. H. Cundiff and P. C. Markunas (Anal. Chem. 33, 1028–1030, 1961).

Example 18
Preparation of the 2,6-dichlorobenzyl ester of hyaluronic acid (HY)

12.4 g of HY tetrabutylammonium salt with a molecular weight of 170,000 corresponding to 20 m.Eq. of a monomeric unit are solubilized in 620 ml of dimethylsulfoxide at 25° C., 5.08 g (21.2 m.Eq.) of 2,6-dichlorobenzyl bromide are added and the solution is kept for 12 hours at 30° C.

The resulting mixture is slowly poured into 3,500 ml of ethyl acetate under constant agitation. A precipitate is formed which is filtered and washed four times with 500 ml of ethyl acetate and finally vacuum dried for 24 hours at 30° C. 9.7 g of the 2,6-dichlorobenzyl ester product in the title are obtained. Quantitative determination of the ester groups is carried out using the method described in Siggia S. and Hanna J. G. "Quantitative organic analysis via functional groups", 4th Edition, John Wiley and Sons, pages 169–172.

Example 19
Preparation of the 4-terbutylbenzyl ester of hyaluronic acid (HY)

12.4 g of HY tetrabutylammonium salt with a molecular weight of 170,000 corresponding to 20 m.Eq. of a monomeric unit are solubilized in 620 ml of dimethylsulfoxide at 25° C., 4.81 g (21.2 m.Eq.) of 4-terbutylbenzyl bromide are added and the solution is kept for 12 hours at 30° C.

The resulting mixture is slowly poured into 3,500 ml of ethyl acetate under constant agitation. A precipitate is formed which is filtered and washed four times with 500 ml of ethyl acetate and finally vacuum dried for 24 hours at 30° C. 9.8 g of the 4terbutylbenzyl ester product in the title are obtained. Quantitative determination of the ester groups is carried out using the method described in Siggia S. and Hanna J. G. "Quantitative organic analysis via functional groups", 4th Edition, John Wiley and Sons, pages 169–172.

Example 20
Preparation of the Heptadecyl ester of hyaluronic acid (HY)

12.4 g of HY tetrabutylammonium salt with a molecular weight of 170,000 corresponding to 20 m.Eq. of a monomeric unit are solubilized in 620 ml of dimethylsulfoxide at 25° C., 6.8 g (21.2 M.Eq.) of Heptadecyl bromide are added and the solution is kept for 12 hours at 30° C.

The resulting mixture is slowly poured into 3,500 ml of ethyl acetate under constant agitation. A precipitate is formed which is filtered and washed four times with 500 ml of ethyl acetate and finally vacuum dried for 24 hours at 30° C. 11 g of the Heptadecyl ester product in the title are obtained. Quantitative determination of the ester groups is carried out using the method described in Siggia S. and Hanna J. G. "Quantitative organic analysis via functional groups", 4th Edition, John Wiley and Sons, pages 169–172.

Example 21
Preparation of the Octadecyl ester of hyaluronic acid (HY)

12.4 g of HY tetrabutylammonium salt with a molecular weight of 170,000 corresponding to 20 m.Eq. of a monomeric unit are solubilized in 620 ml of dimethylsulfoxide at 25° C., 7.1 g (21.2 m.Eq.) of octadecyl bromide are added and the solution is kept for 12 hours at 30° C.

The resulting mixture is slowly poured into 3,500 ml of ethyl acetate under constant agitation. A precipitate is formed which is filtered and washed four times with 500 ml of ethyl acetate and finally vacuum dried for 24 hours at 30° C. 11 g of the octadecyl ester product in the title are obtained. Quantitative determination of the ester groups is carried out using the method described in Siggia S. and Hanna J. G. "Quantitative organic analysis via functional groups", 4th Edition, John Wiley and Sons, pages 169–172.

Example 22

Preparation of the 3-phenylpropyl ester of hyaluronic acid (HY)

12.4 g of HY tetrabutylammonium salt with a molecular weight of 170,000 corresponding to 20 m.Eq. of a monomeric unit are solubilized in 620 ml of dimethylsulfoxide at 25° C. 4.22 g (21.2 m.Eq. ) of 3-phenylpropyl bromide are added and the solution is kept for 12 hours at 30° C.

The resulting mixture is slowly poured into 3,500 ml of ethyl acetate under constant agitation. A precipitate is formed which is filtered and washed four times with 500 ml of ethyl acetate and finally vacuum dried for 24 hours at 30° C. 9 g of the 3-phenylpropyl ester product in the title are obtained. Quantitative determination of the ester groups is carried out using the method described in Siggia S. and Hanna J. G. "Quantitative organic analysis via functional groups", 4th Edition, John Wiley and Sons, pages 169–172.

Example 23

Preparation of the 3,4,5-trimethoxy-benzyl ester of hyaluronic acid (HY)

12.4 g of HY tetrabutylammonium salt with a molecular weight of 170,000 corresponding to 20 M.Eq. of a monomeric unit are solubilized in 620 ml of dimethylsulfoxide at 25° C., 4.6 g (21.2 m.Eq.) of 3,4,5-trimethoxybenzyl chloride are added and the solution is kept for 12 hours at 30° C.

The resulting mixture is slowly poured into 3,500 ml of ethyl acetate under constant agitation. A precipitate is formed which is filtered and washed four times with 500 ml of ethyl acetate and finally vacuum dried for 24 hours at 30° C. 10 g of the 3,4,5-trimethoxybenzyl ester product in the title are obtained. Quantitative determination of the ester groups is carried out using the method described in Siggia S. and Hanna J. G. "Quantitative organic analysis via functional groups", 4th Edition, John Wiley and Sons, pages 169–172.

Example 24

Preparation of the Cinnamyl ester of hyaluronic acid (HY)

12.4 g of Hy tetrabutylammonium salt with a molecular weight of 170,000 corresponding to 20 m.Eq. of a monomeric unit are solubilized in 620 ml of dimethylsulfoxide at 25° C., 4.2 9 (21.2 m.Eq.) of Cinnamyl bromide are added and the solution is kept for 12 hours at 30° C.

The resulting mixture is slowly poured into 3,500 ml of ethyl acetate under constant agitation. A precipitate is formed which is filtered and washed four times with 500 ml of ethyl acetate and finally vacuum dried for 24 hours at 30° C. 9.3 g of the Cinnamyl ester product in the title are obtained. Quantitative determination of the ester groups is carried out using the method described in Siggia S. and Hanna J. G. "Quantitative organic analysis via functional groups", 4th Edition, John Wiley and Sons, pages 169–172.

Example 25

Preparation of the Decyl ester of hyaluronic acid (HY)

12.4 g of HY tetrabutylammonium salt with a molecular weight of 170,000 corresponding to 20 m.Eq. of a monomeric unit are solubilized in 620 ml of dimethylsulfoxide at 25° C., 4.7 g (21.2 m.Eq.) of 1-bromo decane are added and the solution is kept for 12 hours at 30° C.

The resulting mixture is slowly poured into 3,500 ml of ethyl acetate under constant agitation. A precipitate is formed which is filtered and washed four times with 500 ml of ethyl acetate and finally vacuum dried for 24 hours at 30° C. 9.5 g of the Decyl ester product in the title are obtained. Quantitative determination of the ester groups is carried out using the method described in Siggia S. and Hanna J. G. "Quantitative organic analysis via functional groups", 4th Edition, John Wiley and Sons, pages 169–172.

Example 26

Preparation of the Nonyl ester of hyaluronic acid (HY)

12.4 g of HY tetrabutylammonium salt with a molecular weight of 170,000 corresponding to 20 m.Eq. of a monomeric unit are solubilized in 620 ml of dimethylsulfoxide at 25° C. 4.4 g (21.2 mEq.) of 1-bromo nonane are added and the solution is kept for 12 hours at 30° C.

The resulting mixture is slowly poured into 3,500 ml of ethyl acetate under constant agitation. A precipitate is formed which is filtered and washed four times with 500 ml of ethyl acetate and finally vacuum dried for 24 hours at 30° C. 9 g of the Nonyl ester product in the title are obtained. Quantitative determination of the ester groups is carried out using the method described in Siggia S. and Hanna J. G. "Quantitative organic analysis via functional groups", 4th Edition, John Wiley and Sons, pages 169–172.

Complexes of hyaluronic acid and antibiotic drugs—using partial salts of hyaluronic acid with a basic active drug substance component, leaving the residue acid groups of hyaluronic acid free or neutralizing them with metals or bases. These complexes may be represented as:

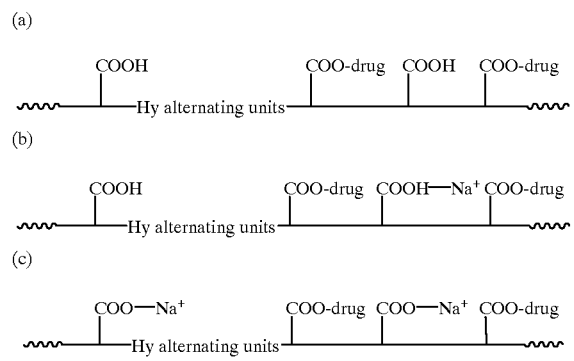

Complexes of hyaluronic acid and antibiotic drugs—using stoichiometrically neutral salts of HY with a basic drug substance component, adding further quantities of the drug component. These can be represented as:

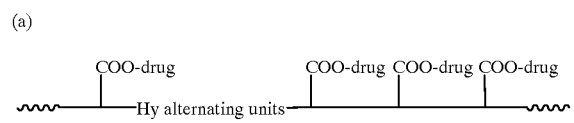

(b) Mixture of:

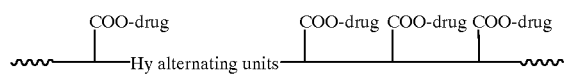

(c) Mixture of:

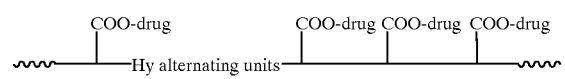

(d) Mixture of:

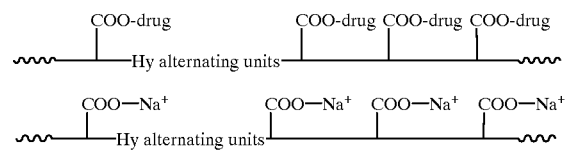

Complexes of hyaluronic acid and antibiotic drugs—using stoichiometrically neutral salts of HY with a basic drug substance component, adding further quantities of the drug component.

Complexes of hyaluronic acid and antibiotic drugs—using stoichiometrically neutral salts of HY with ad libitum mixtures of different drug components. These can be represented as:

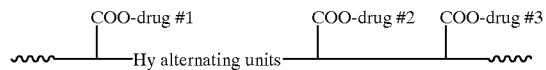

Mixtures of any of the above possible medicaments can also be used in the present invention.

Examples of Active Drug Components

Drugs utilizable in the present invention can be various types, but are basic in nature, existing as a primary, secondary, tertiary, or quaternary amine, whereby the basic amine portion of the drug complexes with the acidic portion of the hyaluronic acid molecule.

Examples of pharmacologically active substances for use in medicaments according to the present invention are: basic and non basic antibiotics, for example aminoglucosidics, macrolides, tetracycline and peptides, such as for example gentanicin, neomycin, streptomycin, dihydrostreptomycin, kanamycin, amikacina, tobramycin, spectinomycin, erythromycin, oleandomycin, carbomycin, spiramycin, oxytetracycline, rolitetracycline, bacitracin, polymyxin B, gramicidin, colistin, chloramphenicol, lincomycin, vancomycin, novobiocin, ristocetin, clindamycin, amphotericin B, griseofulvin, nystatin and possibly their salts, such as sulphates or nitrates, or associations between the same or with other active principles, such as those mentioned hereafter.

Other drugs to be used to advantage according to the present invention are: other anti-infective agents such as diethylcarbamazine, mebendazole, the sulfamides such as sulfacetamide, sulfadiazine, sulfisoxazole; antiviral and antitumoral agents such as iododeoxyuridine, adenine arabinoside, trifluorothymidine, aciclovir, ethyldeoxyuridine, bromovinyldeoxyuridine, and 5-iodo-5'-amino-2', 5'-dideoxyuridine.

Associations or mixtures of such drugs between themselves and possibly with other principles may also be used as antibiotic drugs according to the present invention. If in the place of only one active substance association or mixtures of active substances are used, such as these mentioned above, the salts of the basic active substances and hyaluronic acid and its molecular fractions may be mixed salts of one or more of such basic substances or possibly mixed salts of this type with a certain number of other acid groups of the polysaccharide salified with metals or bases.

Of the antibiotics, the following are of particular note: erythromycin, bacitracin, gentamicin, neomycin, aureomycin, gramicidin and their associations; of the antibacterials and disinfectants: nitrofurazone, mafenids, chlorhexidine, and derivatives of 8-hydroxyquinoline and possibly their salts. This list is of course only for illustrative purposes, and any other antibiotic agents known or described in literature may be used.

Method of Preparing Antibiotic Hyaluronic Acid Salts of the Present Invention

The preparation of the antibiotic salts according to the present invention may be carried out in a manner which is per se known, that is, by combining solutions or suspensions (in water or in organic solvents) of the components in calculated quantities and isolating the salts in an amorphous anhydrous form according to per se known techniques. It is also possible to utilize bases or basic salts with alkaline or alkaline earth metals or magnesium or aluminum or ammonium. It is possible, for example, to (a) first prepare aqueous solutions of the two components, (b) freeze such components from aqueous solutions of their salts with acids of the respective metallic salts (for example sulphates and sodium salts) for treatment with ionic exchangers, and (c) unite the two solutions at a low temperature, for example between 0° and 20°. If the salt thus obtained is easily soluble in water, it should be freeze-dried, while salts which are not easily soluble may be separated by centrifugation, filtration or decantation, and possibly then dessicated.

Example 27

Preparation of the Salt of Hyaluronic Acid (HY) with Streptomycin 2.43 g of streptomycin sulfate (10 mEq) are solubilized in 25 ml of distilled $H_2O$. The solution is eluted in a thermostatic column at 5° C., containing 15 ml of quaternary ammonium resin (Dower 1×8) in $OH^-$ form. The sulfate-free eluate is gathered in a thermostatic container at 5° C.

4.0 g of sodium salt of a hyaluronic acid with a molecular weight of 255,000 (corresponding to 10 mEq of a monomeric unit) are solubilized in 400 ml of distilled $H_2O$. The solution is then eluted in a thermostatic column at 5° C., containing 15 ml of sulfonic resin (Dowex 50×8) in $H^+$ form. The sodium-free eluate is gathered under agitation in the solution of streptomycin base. The resulting solution is frozen and instantly freeze-dried. In the salt thus obtained, all the acidic groups of hyaluronic acid are salified with the basic functions of streptomycin. Yield: 5.5 g.

Microbiological determination on *B. subtilis* ATCC 6633 compared to standard streptomycin showed a content of 33.8% by weight of streptomycin base, corresponding to the theoretically calculated weight. Colorimetric determination of the glucuronic acid combined in polysaccharide according to the method of Bitter et al. (Anal. Biochem. 4, 330, 1962) shows a content in weight of HY acid of 66.2% (theoretical percentage—66.0%).

Example 28
Preparation of the Salt of a Hyaluronic Acid (HY) with Erythromycin 4.0 g of sodium salt of a hyaluronic acid with a molecular weight of 77,000 (corresponding to 10 mEq of a monomeric unit) are solubilized in 400 ml of distilled $H_2O$. The solution is then eluted in a thermostatic column at 5° C., containing 15 ml of sulfonic resin (Dowex 50×8) in $H^+$ form. The eluate, free from sodium, is kept at a temperature of 5° C.

7.34 g of erythromycin base (10 mEq) are added to the solution of HY under agitation at 5° C., until complete solubilization is obtained. The resulting solution is frozen and freeze-dried. In the salt thus obtained all the acidic groups of hyaluronic acid are salified with erythromycin. Yield: 10.8 g.

Microbiological determination on *St. aureus* ATCC 6538 p in comparison with standard erythromycin shows a content of 66.0% by weight in erythromycin base, corresponding to the theoretical value. Colorimetric determination of the glucuronic acid combined in the polysaccharide according to the method of Bitter et al. (Anal. Biochem. 4, 330, 1962) shows a content of HY acid of 34.0%, corresponding to the theoretically calculated percentage.

Example 29
Preparation of the Salt of a Hyaluronic Acid (HY) with Kanamycin 1.46 g of kanamycin sulphate (10 mEq) are solubilized in 25 ml of distilled $H_2O$. The solution is eluted in a thermostatic column at 5° C., containing 15 ml of quaternary ammonium resin (Dowex 1×8) in $OH^-$ form. The eluate, free from sulfates is gathered in a thermostatic container at 5° C.

4. 0 g of the sodium salt of HY with a molecular weight of 165,000 (corresponding to 10 mEq of a monomeric unit) are solubilized in 400 ml of distilled $H_2O$. The solution is then eluted in a thermostatic column at 5° C., containing 15 ml of sulfonic resin (Dowex 50×8) in $H^+$ form. The eluate, free from sodium, is gathered under vortex agitation in the solution of kanamycin base. The solution thus obtained is instantly frozen and freeze-dried. Yield: 4.8 g. In the salt obtained all the acid groups of HY are salified with kanamycin.

Microbiological determination on *B. subtilis* is ATCC 6633 in comparison with standard kanamycin shows a content of 24.2% by weight of kanamycin base, corresponding to the theoretically calculated percentage. Colorimetric determination of the glucuronic acid combined in polysaccharide according to the method of Bitter et al. (Anal. Biochem. 4, 330, 1962) shows a content of HY acid of 75.8% in weight, also corresponding to the theoretical content.

Example 30
Preparation of the Salt of a Hyaluronic Acid (HY) with Neomycin 1.52 g of neomycin sulfate (10 mEq) are solubilized in 20 ml of distilled $H_2O$ and eluted in a thermostatic column at 5° C., containing 15 ml of quaternary ammonium resin (Dowex 1×8) in $OH^-$ form. The eluate, free from sulfates is gathered in a thermostatic container at 5° C.

4.0 g of HY sodium salt with a molecular weight of 170,000 (corresponding to 10 mEq of a monomeric unit) are solubilized in 400 ml of distilled $H_2O$ and eluted in a thermostatic column at 5° C., containing 15 ml of sulfonic resin (Dowex 50×8) in $H^+$ form. The eluate, free from sodium, is gathered under agitation in the solution of neomycin base. The viscoelastic precipitate which forms is separated by decantation and freeze-dried. Yield: 4.76 g. In the salt, all the HY acid groups are salified with neomycin.

Quantitative microbiological determination carried out on *St. aurens* ATCC 6538p compared to standard neomycin shows a content in weight of 21.2% of neomycin base, corresponding to the theoretically calculated value. Colorimetric determination of the glucuronic acid combined in polysaccharide according to the method of Bitter et al. (Anal. Biochem. 4, 330, 1962) shows an HY acid content of 78.8% in weight.

Example 31
Preparation of the Salt of a Hyaluronic Acid (HY) with Gentamicin 1.45 g of gentamicin sulfate (10 mEq) are solubilized in 25 ml of distilled $H_2O$. The solution is eluted in a thermostatic column at 5° C., containing 15 ml of quaternary ammonium resin (Dowex 1×8) in $OH^-$ form. The eluate, free from sulfates, is gathered in a thermostatic container at 5° C.

4.0 g of sodium salt of HY with a molecular weight of 170,000 (corresponding to 10 mEq of a monomeric unit) are solubilized in 400 ml of distilled $H_2O$. The solution is then eluted in a thermostatic column at 5° C., containing 15 ml of sulfonic resin (Dowex 50×8) in $H^+$ form. The eluate, free from sodium, is gathered under agitation in a vortex in the solution of gentamicin base. The thick and very viscous precipitate which form is separated by decantation and freeze-dried. Yield: 4.65 g. In the salt thus obtained, all the HY acid groups are salified with gentamicin.

Quantitative microbiological determination carried out on *S. epidermidus* ATCC 12228 compared to standard gentamicin shows a content in weight of 20.0% of gentamicin base, corresponding to the theoretical content. Colorimetric determination of the glucuronic acid combined in polysaccharide according to the method of Bitter et al. (Anal. Biochem. 4, 330, 1962) shows an HY acid content of 80.0%.

Example 32
Preparation of the Salt of a Hyaluronic Acid (HY) with Amikacin 1.47 g of amikacin sulfate (10 mEq) are solubilized in 100 ml of distilled $H_2O$ at 50° C.

4.0 g of sodium salt of HY with a molecular weight of 170,000 (corresponding to 10 mEq of a monomeric unit) are solubilized in 400 ml of distilled $H_2O$. The solution is then eluted in a thermostatic column at 5° C., containing 15 ml of sulfonic resin (Dowex 50×8) in $H^+$ form.

The eluate, free from sodium, is gathered under agitation in a vortex in the solution of amikacin base. The thick and extremely viscous precipitate which forms is separated by decantation and freeze-dried. Yield: 5.16 g.

In the salt thus obtained, all the HY acid groups are salified with amikacin.

Quantitative microbiological determination carried out on *St. aureus* ATCC 29737 in comparison to standard amikacin shows a content of 27.7% in weight in amikacin base, corresponding to the theoretical content. Colorimetric determination of the glucuronic acid combined in polysaccharide according to the method of Bitter et al. (Anal. Biochem. 4, 330, 1962) shows an HY acid content of 72.3% in weight.

Example 33
Preparation of the Salt of a Hyaluronic Acid (HY) with Rolitetracycline 4.0 g of HY sodium salt with a molecular weight of 170,000 (corresponding to 10 mEq of a monomeric unit) are solubilized in 400 ml of distilled $H_2O$. The solution is then eluted in a thermostatic column at 5° C., containing 15 ml of sulfonic resin (Dowex 50×8) in $H^+$ form. The eluate, free from sodium, is kept at a temperature of 5° C.

5.3 g of rolitetracycline base (10 mEq) are added to the solution of HY acid under agitation at 5° C., away from the light, until complete solubilization has been achieved. The solution thus obtained is instantly frozen and freeze-dried. Yield: 8.9 g. In the salt thus obtained, all the HY acid groups are salified with rolitetracycline.

Microbiological determination on *B. pumilus* ATCC 14884 in comparison to standard rolitetracycline shows a content of 58.2% in weight in rolitetracycline base, corresponding to the theoretical value. Colorimetric determination of the glucuronic acid combined in polysaccharide according to the method of Bitter et al. (Anal. Biochem. 4, 330, 1962) shows an HY acid content of 41.8% in weight.

Example 34
Preparation of the Salt of a Hyaluronic Acid (HY) with Polymyxin B 2.4 g of polymyxin B base (10 mEq) are suspended in 100 ml of distilled $H_2O$ at 5° C.

4.0 g of HY sodium salt with a molecular weight of 170,000 (corresponding to 10 mEq of a monomeric unit) are solubilized in 400 ml of distilled $H_2O$. The solution is then eluted in a thermostatic column at 5° C., containing 15 ml of sulfonic resin (Dowex 50×8) in $H^+$ form. The eluate, free from sodium, is gathered under vigorous agitation in the suspension of polymyxin base at 5° C. After an initial phase during which the solution becomes clear, there is a progressive formation of a not easily soluble product which is completely precipitated by 5 volumes of acetone. The precipitate is filtered, washed with acetone and then vacuum dried. Yield: 6.05 g. In the salt thus obtained, all the HY acid groups are salified with polymyxin B.

Quantitative microbiological determination carried out on *B. bronchiseptica* ATCC 4617 in comparison to standard polymyxin B shows a content of 38.7% in polymyxin B base, corresponding to the theoretical value. Colorimetric determination of the glucuronic acid combined in polysaccharide according to the method of Bitter et al. (Anal. Biochem. 4, 330, 1962) shows an HY acid content of 61.3%.

Example 35
Preparation of the Salt of a Hyaluronic Acid (HY) with Gramicidin S 6.7 g of gramicidin S hydrochloride (10 mEq) are suspended in 200 ml of ethanol/$H_2O$, 80:20, v/v. The solution is then eluted in a thermostatic column at 5° C., containing 15 ml of quaternary ammonium resin (Dowex 1×8) in $OH^-$ form.

4.0 g of the sodium salt of HY with a molecular weight of 165,000 (corresponding to 10 mEq of a monomeric unit) are solubilized in 400 ml of distilled $H_2O$. The solution is then eluted in a thermostatic column at 5° C., containing 15 ml of sulfonic resin (Dowex 50×8) in $H^+$ form. 200 ml of DMSO are added to the eluate, free from sodium, and the mixture is kept under agitation at 5° C. The solution of gramicidin base is then slowly added. The resulting solution is precipitated by 10 volumes of acetone. The precipitate is filtered, washed with acetone and vacuum dried. Yield: 9.55 g. In the salt thus obtained, all the HY acid groups are salified with gramicidin S.

Quantitative microbiological determination carried out on *S. faecium* ATCC 10541 in comparison to standard gramicidin S shows a content of 60.0% of gramicidin S base, corresponding to the theoretically value. Colorimetric determination of the glucuronic acid combined in polysaccharide according to the method of Bitter et al. (Anal. Biochem. 4, 330, 1962) shows an HY acid content of 40.0%.

Example 36
Preparation of the Salt of a Hyaluronic Acid (HY) with Neomycin and with Polymyxin 4.0 g of the HY sodium salt with a molecular weight of 170,000 (corresponding to 10 mEq of a monomeric unit) are solubilized in 400 ml of distilled $H_2O$. The solution is eluted in a thermostatic column at 5° C., containing 15 ml of sulfonic resin (Dowex 50×8) in $H^+$ form. The eluate, free from sodium, is gathered in a thermostatic container at 5° C. 0.150 g of Polymyxin B base (0.63 mEq) are added under vigorous agitation. 1.425 g of Neomycin sulphate (9.37 mEq) are solubilized in 25 ml of distilled $H_2O$. The solution is eluted in a thermostatic column at 5° C., containing 15 ml of quaternary ammonium resin (Dowex 1×8) in $OH^-$ form.

The eluate, free from sulphates, is gathered under vigorous agitation in the solution of HY acid and Polymyxin B. The precipitate which forms is separated by centrifugation and vacuum dried. Yield: 4.85 g. 17.25 mg of this product contain:

NEOMYCIN equal to 5.0 mg of NEOMYCIN SULPHATE

POLYMYXIN B equal to 0.63 mg (about 5000 UI) of POLYMYXIN SULPHATE

N.B. Determinations were carried out after separation by HPLC of the two active principles.

Example 37
Preparation of the Salt of a Hyaluronic Acid (HY) with Streptomycin and with Sodium 98.68 g of HY sodium salt with a molecular weight of 255,000 (corresponding to 246 mEq of a monomeric unit) are solubilized in 8.5 l of distilled $H_2O$. The solution is then eluted in a thermostatic column at 5° C., containing 300 ml of sulfonic resin (Dowex 50×8) in $H^+$ form. The eluate, free from sodium, is gathered in a thermostatic container at 5° C.

1.88 g of Streptomycin sulphate (7.74 mEq) are solubilized in 20 ml of distilled $H_2O$. The solution is then eluted in a thermostatic column at 5° C., containing 12 ml of quaternary ammonium resin Dowex 1×8) in $OH^-$ form. The eluate, free from sulphates, is gathered under agitation in the solution of HY acid. 238.3 ml of a solution of 1 M NaOH are slowly added under agitation and the resulting solution is instantly frozen and freeze-dried. Yield: 99.8 g. 100 g of the product contain 1.5 g of Streptomycin as a base.

Example 38

A paste comprising the 25% benzyl ester of hyaluronic acid, HYAFF 11p25, having a molecular weight between 160,000 and 230,000 Daltons, and granules of hydroxyapatite with a nominal diameter of 420 to 1,000 $\mu$m, was obtained in the following manner.

5 grams of HYAFF 11p25, sterilized using gamma rays at an intensity of 1.25 Mrad, were added to 50 grams of sterilized water. The system was treated in a double spiral mixer at 40 rpm. The temperature was kept at 30° C. ±2° C., and solubilization was performed for 8 hours. The solution was then placed in a high vacuum for 2 hours at 0.01 mbar to eliminate the dissolved air. The resulting viscosity was 23 Pa.s.

Subsequently, to 1 gr of solution was added 0.5 gr of commercially available hydroxyapatite ("INTERPORE200") and the mixture was stirred by hand with a spatula until a homogeneous paste was obtained. The granules proved to be bound together, forming a material which was easy to insert into cavities without the risk of the granular bone replacement becoming dislodged, either during or after the operation.

Example 39

A paste comprising the 50% ethyl ester of hyaluronic acid, HYAFF 7p50, with a molecular weight of between 140,000 and 210,000 Daltons, and granules of hydroxyapatite with a nominal diameter of 420 to 1000 μm, was obtained as follows.

7 grams of HYAFF 7p50, sterilized using gamma rays at an intensity of 1.25 Mrad, were added to 50 grams of sterilized water. The system was treated in a double spiral mixer at a speed of 40 rpm. The temperature was kept at 40° C.±2° C., and solubilization was performed for 8 hours. After solubilization, the solution was placed in a vacuum at 0.01 mbar for 2 hours to eliminate any dissolved air. The resulting viscosity was 25 Pa.s.

Subsequently, to 1 gr of this solution was added 0.4 gr of commercially available hydroxyapatite ("INTERPORE200"), and the mixture was stirred by hand with a spatula until a homogeneous paste was obtained. The granules proved to be bound together, forming a material which was easy to insert into cavities without the risk of the granular bone replacement becoming dislodged, either during or after the operation.

Example 40

A paste comprising a mixture of 50% benzyl esters of hyaluronic acid, HYAFF 11p50, with a molecular weight between 140,000 and 250,000 Daltons, and granules of porous calcium carbonate with a pore size of 630 μm to 1000 μm, was obtained as follows.

6 grams of HYAFF 11p50, sterilized using gamma rays at an intensity of 1.25 Mrad, were added to 50 grams of sterilized water. The system was treated in a double spiral mixer at a speed of 40 rpm. The temperature was kept at 40° C.±2° C., and solubilization, was performed for 6 hours. After solubilization, the solution was maintained for 2 hours in a high vacuum at 0.01 mbar to eliminate any air. The resulting viscosity was 21 Pa.s.

Subsequently, to 1 gr of solution was added 0.6 gr of commercially available calcium carbonate ("BIOCORAL 1000"), and this was stirred by hand with a spatula until a homogeneous paste was obtained. The granules proved to be bound together, forming a material which was easy to insert into cavities without the risk of the granular bone replacement becoming dislodged, either during or after the operation.

Example 41

A paste containing hyaluronic acid with a molecular weight of 140,000–180,000 Daltons and granules of hydroxyapatite with a nominal diameter size of 420–1000 μm was obtained in the following manner:

7 gr of hyaluronic acid, sterilized by filtration, were added to 50 gr of sterilized water. The system was treated in a double sprial mixer at 40 rpm. The temperature was kept at 25° C. and solubilization was performed for 16 hours. the solution was then placed under high vacuum for 2 hours to eliminate the dissolved air. The resulting viscosity was 24.7 Pa.s.

Subsequently, to 1 gr of solution was added 0.4 qr of commercially available hydroxyapatite (Interpore 200) and the mixture was stirred by hand with a spatula until a homogeneous paste was obtained. The granules proved to be bound together, forming a material which was easy to insert into cavities without the risk of the granular bone replacement becoming dislodged, either during or after the operation.

Animal Model and Treatment

In order to enhance retention of hydroxyapatite particles and to promote ease of handling, the above-mentioned preparation was used to fill fresh tooth extraction sites in canines. Beagle dogs were used as the animal model. Maxillary and mandibular incisors and premolars were removed, so that each animal received 12 defects, six in the maxilla, six in the mandible. Subsequently, the interradicular septum was removed to increase the volume of the defect. The extraction sites were implanted with the above-mentioned preparation, left empty, or filled with hydroxyapatite granules as controls. Simple suturing was used to bring the gingival flaps together. Animals were sacrificed 1, 2 and 3 months after surgery. At the time of sacrifice, tissue fixation was performed using the perfusion technique through incannulation of the maxillary artery and injection of Karnowsky fixative.

This study showed the ease of use of hyaluronic acid-hydroxyapatite composites to fill fresh tooth extraction sites. The mixture can be manually inserted or injected under pressure into a bone defect in situ. Retention of particles was achieved; with time, the bonding solution was resorbed, and bone ingrowth progressed.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A paste for a granular bone replacements comprising a bonding solution of a 50% benzyl ester of hyaluronic acid having a molecular weight between about 140,000 Daltons and about 250,000 Daltons, and granules of hydroxyapatite having a diameter of from about 630 μm to about 1,000 μm.

* * * * *

UNITED STATES PATENT AND TRADEMARK OFFICE
CERTIFICATE OF CORRECTION

PATENT NO. : 6,533,820 B2
DATED : March 18, 2003
INVENTOR(S) : Franco Dorigatti et al.

It is certified that error appears in the above-identified patent and that said Letters Patent is hereby corrected as shown below:

<u>Title page,</u>
Please insert the following information:
-- Related U.S. Application Data
[63] This application is a divisional of U.S. Applicaton No. 08/318,859, abandoned, which is the National Stage of International Application No. PCT/EP93/00933, filed April 16, 1993 --; and
-- [30] Foreign Application Priority Data
April 17, 1992  [IT]    Italy………………………..PD92A000072 --

Signed and Sealed this

Sixteenth Day of December, 2003

JAMES E. ROGAN
*Director of the United States Patent and Trademark Office*